(12) United States Patent
Rusko et al.

(10) Patent No.: US 11,581,087 B2
(45) Date of Patent: Feb. 14, 2023

(54) METHOD, SYSTEM AND COMPUTER READABLE MEDIUM FOR AUTOMATIC SEGMENTATION OF A 3D MEDICAL IMAGE

(71) Applicant: GE Precision Healthcare LLC, Wauwatosa, WI (US)

(72) Inventors: Laszlo Rusko, Budapest (HU); Elisabetta Grecchi, Chalfont St. Giles (GB); Petra Takacs, Budapest (HU)

(73) Assignee: GE Precision Healthcare LLC, Wauwatosa, WI (US)

( * ) Notice: Subject to any disclaimer, the term of this patent is extended or adjusted under 35 U.S.C. 154(b) by 125 days.

(21) Appl. No.: 17/064,680

(22) Filed: Oct. 7, 2020

(65) Prior Publication Data
US 2021/0125707 A1    Apr. 29, 2021

Related U.S. Application Data

(60) Provisional application No. 62/924,864, filed on Oct. 23, 2019.

(30) Foreign Application Priority Data

Jan. 23, 2020 (EP) .................................. 20153471

(51) Int. Cl.
*G06T 7/00* (2017.01)
*G16H 30/40* (2018.01)
(Continued)

(52) U.S. Cl.
CPC ............... *G16H 30/40* (2018.01); *G06N 3/08* (2013.01); *G06T 7/0012* (2013.01); *G06T 7/10* (2017.01);
(Continued)

(58) Field of Classification Search
CPC .......... G16H 30/40; G16H 50/20; G06N 3/08; G06N 3/0454; G06T 7/0012; G06T 7/10;
(Continued)

(56) References Cited

U.S. PATENT DOCUMENTS 10,621,720 B2 * 4/2020 Pheiffer ................. G06T 7/0012
2013/0308849 A1 * 11/2013 Fei .......................... G06T 7/0012
382/131

(Continued)

FOREIGN PATENT DOCUMENTS

WO    2017210690 A1    12/2017
WO    WO-2017210690 A1 * 12/2017

OTHER PUBLICATIONS

Liu et al. "Cascaded coarse-to-fine convolutional neural networks for pericardial effusion localization and segmentation on CT scans," 2018 IEEE 15th International Symposium on Biomedical Imaging (ISBI 2018), IEEE, Apr. 4, 2018 (Apr. 4, 2018), 1092-1095, (Year: 2018).*

(Continued)

*Primary Examiner* — Van D Huynh

(57) ABSTRACT

A method, a system and a computer readable medium for automatic segmentation of a 3D medical image, the 3D medical image comprising an object to be segmented, the method characterized by comprising: carrying out, by using a machine learning model, in at least two of a first, a second and a third orthogonal orientation, 2D segmentations for the object in slices of the 3D medical image to derive 2D segmentation data; determining a location of a bounding box (10) within the 3D medical image based on the 2D segmentation data, the bounding box (10) having predetermined dimensions; and carrying out a 3D segmentation for the object in the part of the 3D medical image corresponding to the bounding box (10).

15 Claims, 5 Drawing Sheets

(51) Int. Cl.
*G06T 7/10* (2017.01)
*G06N 3/08* (2023.01)

(52) U.S. Cl.
CPC .............. *G06T 2207/20081* (2013.01); *G06T 2207/20084* (2013.01); *G06T 2207/30004* (2013.01); *G06T 2210/12* (2013.01)

(58) Field of Classification Search
CPC .......... G06T 2207/20081; G06T 2207/20084; G06T 2207/30004; G06T 2210/12; G06T 2207/10088; G06T 7/11
USPC ....................................................... 382/128
See application file for complete search history.

(56) References Cited

U.S. PATENT DOCUMENTS

| | | | | |
|---|---|---|---|---|
| 2018/0315188 | A1* | 11/2018 | Tegzes | G06T 7/11 |
| 2019/0205606 | A1* | 7/2019 | Zhou | G06N 3/0445 |
| 2020/0342600 | A1* | 10/2020 | Sjöstrand | G06T 15/08 |
| 2021/0233247 | A1* | 7/2021 | Cao | G06N 3/08 |

OTHER PUBLICATIONS

Payer et al., "Multi-label Whole Heart Segmentation Using CNNs and Anatomical Label Configurations" In: "Pervasive: International Conference on Pervasive Computing", Sep. 14, 2017 (Sep. 14, 2017), Springer, Berlin, Heidelberg 032548, XP055486743, ISBN: 978-3-642-17318-9 vol. 10663, pp. 190-198 (Year: 2017).*

Li et al., "MDS-Net: A Model-Driven Stack-Based Fully Convolutional Network for Pancreas Segmentation", arxiv.org, Cornell University Library, 201 Olin Library Cornell University Ithaca, NY 14853, Mar. 3, 2019 (Mar. 3, 2019), XP081549124, 12 pages. (Year: 2019).*

Akkus et al. "Deep learning for brain MRI segmentation: state of the art and future directions. Journal of digital imaging," 2017, 30.4: 449-459., 11 pages.

Bernal et al. "Quantitative analysis of patch-based fully convolutional neural networks for tissue segmentation on brain magnetic resonance imaging." arXiv preprint arXiv:1801.06457, 2018., 10 pages.

De Jong et al., "Strongly reduced volumes of putamen and thalamus in Alzheimer's disease: an MRI study." Brain, 2008, 131.12: 3277-3285, 9 pages.

De Vos et al., "ConvNet-Based Localization of Anatomical Structures in 3D Medical Images", arxiv.org, Cornell University Library, 201 Olin Library Cornell University Ithaca, NY 14853, Apr. 19, 2017 (Apr. 19, 2017), XP080763925, DOI: 10.1109/TMI.2017.2673121, 12 pages.

Dolz et al., "3D fully convolutional networks for subcortical segmentation in MRI: A large-scale study." NeuroImage, 2018, 170: 456-470, 15 pages.

European application No. 20153471.6 filed Jan. 23, 2020—European extended Search Report dated Jul. 7, 2020; 14 pages.

Fox et al., "Brain atrophy progression measured from registered serial MRI: validation and application to Alzheimer's disease." Journal of Magnetic Resonance Imaging, 1997, 7.6: 1069-1075.

Jin et al: "RA-UNet: A hybrid deep attention-aware network to extract liver and tumor in CT scans", arxiv.org, Cornell University Library, 201 Olin Library Cornell University Ithaca, NY 14853, Nov. 4, 2018 (Nov. 4, 2018), XP080941962, 13 pages.

Karani et al., "A lifelong learning approach to brain mr segmentation across scanners and protocols." In: International Conference on Medical Image Computing and Computer-Assisted Intervention. arXiv preprint arXiv:1801.06457, 2018, 8 pages.

Li et al., "MDS-Net: A Model-Driven Stack-Based Fully Convolutional Network for Pancreas Segmentation", arxiv.org, Cornell University Library, 201 Olin Library Cornell University Ithaca, NY 14853, Mar. 3, 2019 (Mar. 3, 2019), XP081549124, 12 pages.

Liu et al. "Cascaded coarse-to-fine convolutional neural networks for pericardial effusion localization and segmentation on CT scans," 2018 IEEE 15th International Symposium on Biomedical Imaging (ISBI 2018), IEEE, Apr. 4, 2018 (Apr. 4, 2018), 1092-1095, XP033348339, DOI: 10.1109/ISBI.2018.8363761, 4 pages.

Payer et al., "Multi-label Whole 4-6 Heart Segmentation Using CNNs and Anatomical Label Configurations" In: "Pervasive: International Conference on Pervasive Computing", Sep. 14, 2017 (Sep. 14, 2017), Springer, Berlin, Heidelberg 032548, XP055486743, ISBN: 978-3-642-17318-9 vol. 10663, pp. 190-198, DOI: 10.1007/978-3-319-75541-0 20, 8 pages.

\* cited by examiner

METHOD, SYSTEM AND COMPUTER READABLE MEDIUM FOR AUTOMATIC SEGMENTATION OF A 3D MEDICAL IMAGE

FIELD OF THE INVENTION

The subject matter disclosed herein relates to a method, a system and a computer readable medium for automatic segmentation of a 3D medical image using a machine learning model. More particularly, the disclosed subject matter relates to image processing, and to systems and methods for medical imaging with efficient and accurate three-dimensional 3D image segmentation capabilities.

BACKGROUND OF THE INVENTION

Segmentation of anatomical structures, e.g. organs in 3D medical images is a fundamental task in a number of clinical processes in the field of oncology, radiology and in planning surgical interventions. A 3D medical image is a medical image of a 3D volume in a subject along an orientation such as axial, coronal, sagittal, or oblique, where the medical images may be acquired by a 2D acquisition, a 3D acquisition, or a combination thereof. These 3D medical images can be considered as a set of 2D slices or layers in each of the 3D directions, i.e. a set of 2D axial, coronal or sagittal slices or more generally, a set of 2D slices in any of a first, a second and a third orthogonal orientation. In the present context, the term 'first, second and third orthogonal orientations' comprises all possible sets of three-dimensional orientations. Exemplary techniques for imaging include conventional ultrasound imaging, computed tomography ("CT") imaging, magnetic resonance imaging ("MR" or "MRI"), and nuclear medicine imaging techniques, such as positron emission tomography ("PET") and single photon emission computed tomography ("SPECT"). Segmentation is used to measure the size and shape of anatomical structures, to guide spatial normalization of anatomy between individuals and to plan medical interventions. The spectrum of available segmentation approaches is broad, ranging from manual outlining of structures in 2D cross-sections to more developed methods that use a so called 'registration' to find optimal correspondences between 3D images and a labeled probability map or atlas. There are also known semiautomatic approaches that combine the efficiency and repeatability of automatic segmentation with the human judgment that can only come from skilled expertise.

Despite the fact that a large number of fully automatic and semiautomatic segmentation methods have been disclosed, still manual delineation is generally used as the technique of choice for image segmentation. Reluctance to use the fully automatic approach is due to the concerns about its insufficient reliability in cases where the target anatomy may difference from the norm, as well as due to high computational demands of the approach based on image registration.

Manually tracing the outlines on a contiguous set of 2D slices and then combining them can be time consuming and labor intensive. Time and labor increase significantly both as the number of image slices increase, and as a number and size of an organ, tumor, etc. in an anatomical area of interest increases. Quality of the outlining and quality of a produced 3D object depend on a resolution and contrast of the 2D slices, and on knowledge and judgment of the clinician performing the reconstruction.

Using reliable automatic image segmentation could save time and labor, and could increase precision by eliminating subjectivity of the clinician.

Automated image segmentation of organs faces certain challenges. Some organs are located in a soft tissue environment wherein resolution against surrounding structures has poor contrast since neighboring organs have similar density values. Furthermore, shape and position of organs may change periodically. Imaging parameters of imaging machines vary as well.

Segmentation is the process of assigning labels to individual voxels in the data set of the 3D medical image. Automatic segmentation thereby means automated recognition and labeling of human anatomical structures in 2D or 3D digital scans of the human body.

For example, magnetic resonance imaging ("MR") is widely used for analyzing brain structures due to its high contrast for soft tissues, proper spatial resolution and to its non-invasive character. MRI brain analysis can be used for assessment of brain disorder such as Alzheimer's disease and other neurological diseases causing tissue atrophy (see e.g.: FOX, Nick C.; FREEBOROUGH, Peter A. Brain atrophy progression measured from registered serial MM: validation and application to Alzheimer's disease. Journal of Magnetic Resonance Imaging, 1997, 7.6: 1069-1075.). For quantifying atrophies, proper segmentation and measurements of brain tissues are needed, as precise detection and localization of the damaged structures are important for diagnosis and therapy planning (see e.g.: AKKUS, Zeynettin, et al. Deep learning for brain MRI segmentation: state of the art and future directions. Journal of digital imaging, 2017, 30.4: 449-459.). Another clinical application of MR image segmentation is radiation therapy planning (RTP) that requires precise contouring of the organs at risk surrounding the tumor to be irradiated.

As mentioned above, at this moment manual contouring is the gold standard for organ segmentation, which requires contouring various structures slice by slice, which is a time consuming, expensive activity and can be inaccurate due to human errors. The need for precise segmentation tools is unquestionable. Deep learning methods can bridge the limitations of traditional machine learning tools which are weaker at generalizing, so the use of convolutional neural networks (CNNs) is frequently proposed in medical image analysis (see e.g.: DOLZ, Jose; DESROSIERS, Christian; APED, Ismail Ben. 3D fully convolutional networks for subcortical segmentation in MRI: A large-scale study. NeuroImage, 2018, 170: 456-470.).

There is a special need to segment various organs or particular anatomical structures or parts—generally called as objects—inside the brain which are relevant for assessment of Alzheimer's disease (Amygdala, Caudate, Hippocampus, Putamen, Thalamus). Volumes of putamen and thalamus were significantly reduced in patients diagnosed with probable Alzheimer's disease, and other changes are also visible on the organs of basal ganglia (see e.g.: DE JONG, Laura W., et al. Strongly reduced volumes of putamen and thalamus in Alzheimer's disease: an MRI study. Brain, 2008, 131.12: 3277-3285.). The damage initially appears to take place in the hippocampus and the entorhinal cortex, parts of the brain essential in forming memories. As more neurons die, additional parts of the brain are affected and begin to shrink. Alzheimer's disease gradually leads to nerve cell death and tissue loss throughout the brain. Over time, the brain shrinks dramatically, affecting nearly all its functions. With detecting changes in the proper brain parts in the earlier stage of the Alzheimer's disease the medical treatment can be started and symptoms of the disease (such as decreased anamnesis, awareness and cognitive abilities) can be softened and slowed down.

The difficulties in segmenting smaller organs inside the brain is the image resolution and the low contrast between neighboring tissues, so one can mainly trust on relative localization based on larger, better separable organs; for example, the ventricle is relevant as the examined organs of the basal ganglia are located next to it. There exists a special need to accurately segment these organs.

There are prior art solutions for segmenting organs like above, which propose to increase accuracy and reliability by means of two-step or multi-step processes.

In Vanya V. Valindria, et al.: Small Organ Segmentation in Whole-body MRI using a Two-stage FCN and Weighting Schemes (MICCAI Workshop on Machine Learning in Medical Imaging (MLMI) 2018, arXiv:1807.11368v1 [cs.CV] 30 Jul. 2018) a two-stage approach is disclosed, according to which a coarse-scale segmentation is trained to a CNN to deal with the multi-organ segmentation, and then a fine-scale segmentation focuses only to a 3D bounding box, corresponding to a cropped region of interest (ROI) of the specific organ, selected in the coarse segmentation. The fine-scale segmentation is carried out by a separate CNN trained for that specific fine-scale stage. The drawback of this solution is that both of the two stages are carried out in 3D, resulting in a high computational demand; the coarse-scale segmentation, which is only a preliminary or preparational stage of the effective segmentation stage necessitates considerable computer resources due to its 3D character.

A three-step localization/segmentation process is disclosed in Haibin Chen, et al.: A Recursive Ensemble Organ Segmentation (REOS)/Framework: Application in Brain Radiotherapy (Phys Med Biol. 2019 Jan. 11; 64(2):025015. doi: 10.1088/1361-6560/aaf83c.). This method has the same drawbacks as mentioned above.

These known methods do not solve the problems of resource-efficient and reliable automatic segmentation, especially for segmentation of brain MR images, where the above mentioned difficulties arise.

Thus, there is a need for a solution allowing an improvement over existing methods and systems. There is a need for automatic segmentation method, computer program and system eliminating as much as possible the shortcomings of known techniques. There is a particular need for an automatic segmentation method allowing an efficient and reliable localization of the region of interest with relatively low computational needs, and a subsequent fine 3D segmentation.

SUMMARY OF THE INVENTION

In an exemplary embodiment, a method is provided for automatic segmentation of a 3D medical image, the 3D medical image comprising an object to be segmented, the method characterized by comprising: carrying out, by using a machine learning model, in at least two of a first, a second and a third orthogonal orientation, 2D segmentations for the object in slices of the 3D medical image to derive 2D segmentation data; determining a location of a bounding box within the 3D medical image based on the 2D segmentation data, the bounding box having predetermined dimensions; and carrying out a 3D segmentation for the object in the part of the 3D medical image corresponding to the bounding box.

In another exemplary embodiment, a system is provided for automatic segmentation of a 3D medical image, the 3D medical image comprising an object to be segmented, the system characterized by comprising: a 2D segmentation unit using a machine learning model and being configured to carry out, in at least two of a first, a second and a third orthogonal orientation, 2D segmentations for the object in slices of the 3D medical image to derive 2D segmentation data; a determining unit configured to determine a location of a bounding box within the 3D medical image based on the 2D segmentation data, the bounding box having predetermined dimensions; and a 3D segmentation unit being configured to carry out a 3D segmentation for the object in the part of the 3D medical image corresponding to the bounding box.

In a further exemplary embodiment, a computer readable medium is provided, the computer readable medium comprising instructions which, when executed by a computer, cause the computer to carry out the above method.

An automatic segmentation method according to the subject matter disclosed herein can decrease the processing time and/or resources and make possible to establish an efficient localization of the bounding box of the region of interest. The automatic segmentation disclosed herein is proved to be accurate and robust not requiring any post editing, and successfully eliminating the problems related to inter- and intra-operator variability.

BRIEF DESCRIPTION OF THE DRAWINGS

Characteristics, objectives and advantages of embodiments of the subject matter will become apparent from the following description, which is given solely by way of illustration and is non-limiting, and is to be read with reference to the appended drawings in which.

DETAILED DESCRIPTION OF THE INVENTION

The subject matter disclosed herein is a method based on a machine learning model, e.g. on a deep-learning technique. In the following, an exemplary image dataset is described for use in the method, as well as an exemplary suitable architecture, and exemplary details of the training.

Image Dataset

The exemplary image dataset was collected for a study on Alzheimer's disease. All images were standard T1 images (T1-weighted scans produced by MRI using short Time to Echo and Repetition Time values) depicting the brain and small part of the neck. All images were preprocessed with an available tool that transforms images into a common geometry (orientation, resolution, uniform voxel size) and applies atlas to segment several structures in the brain. The automatically segmented contours (used for both model training and evaluation) were not verified by medical doctors, so they can be only considered 'pseudo-gold' segmentations.

Additional pre-processing was applied—which is an option in the disclosed example—to the image dataset including the following. First, the voxel size was normalized to be nearly equal to 1×1×1 mm (using integer factor for up or down-sampling). Then, the images were cropped or padded with zero voxels to get 256×256×256 resolution. Finally, min-max normalization was applied to intensity values, such that the intensity belonging to 99.9 histogram percentile was used instead of the global intensity maximum.

The image dataset was processed with the subject matter disclosed herein, which is a method for automatic segmentation of a 3D medical image using a machine learning model. In an embodiment deep learning neural network model is used for this purpose, however other types of machine learning models may also be applicable. The 3D medical image comprises an object to be segmented. The image of the object, being e.g. an organ or a particular part or anatomical structure of the human body, may extend only to a certain part of the entire 3D medical image, therefore, a localization is applied as a preparation for the effective segmentation.

Figure 1:
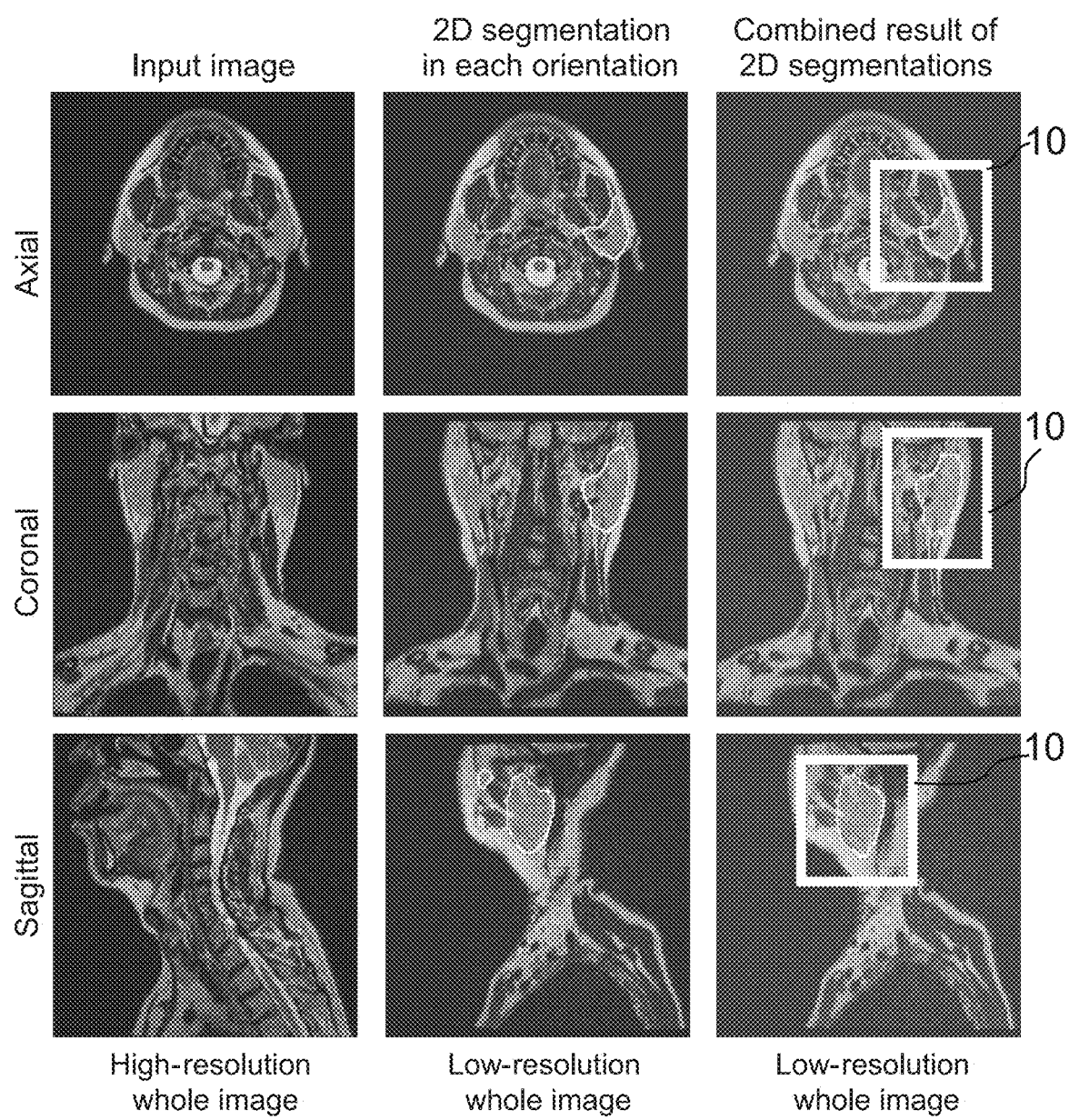
FIG. 1 illustrates a first stage of an embodiment of the automated segmentation.

The method is therefore a two-stage process, wherein a first stage is depicted in FIG. 1, the first stage serving for locating a region of interest, practically a bounding box 10 within the 3D medical image. In this first stage, on axial, coronal and sagittal slices (or layers) of an input image depicted in the first column of FIG. 1, 2D segmentations are carried out for the object, the results of which are depicted in the second column of FIG. 1 with respective white contours. Instead of the axial, coronal and sagittal orientations, any suitable first, second and third orthogonal orientations can be used.

The depicted example comprises 2D segmentations in all the three orthogonal orientations, however, carrying out the 2D segmentations in at least two of the three orthogonal orientations may also be suitable and sufficient for a combined evaluation for accurately locating the bounding box 10. In this latter case, only two respective values are evaluated in combination for each respective voxel of the 3D medical image, instead of three, in the same way as detailed below in connection with the depicted example. Both options are within the scope of the subject matter disclosed herein.

The 2D segmentations derive 2D segmentation data, being probability values in an embodiment, as detailed later on. On the basis of the fused (or combined) evaluation of the 2D segmentation data in the axial, coronal and sagittal orientations, being represented as respective white shape contours of the object in the third column of FIG. 1, a location of a bounding box 10 (see also FIG. 2) is determined within the 3D medical image. The latter is depicted as white rectangles in the third column, also indicating the size and position of the bounding box 10 in the three orthogonal planes. The dimensions of the bounding box 10 are predetermined based on a-priori information relating to the object (i.e. organ or body part) to be segmented and/or the image dataset.

It is conceivable that FIG. 1 may only depict the most characteristic slice or layer of each of the particular orientations, i.e. that those with the largest segmented area outlines.

The second and third columns of FIG. 1 indicate 'low-resolution whole image', which means that the 2D segmentations can be carried out in a resolution which is reduced with respect to the full resolution of the 3D medical image. Resolution can be reduced in all or any subset of the dimensions of the 3D medical image, e.g. by generating a reduced resolution 3D image or by carrying out 2D segmentations only for a subset of slices (e.g. every second, third, etc.) in all or any subset of the orientations. In this way, computational load of the 2D segmentations can be further reduced, while the combined results thereof provide a sufficient accuracy for locating the bounding box 10, as detailed in the following.

The above combined localization may also be called as 2.5D localization, which is implemented by training 2D models on axial, coronal and sagittal planes, or more generally, on planes in the first, second and third orthogonal orientations, fusing their prediction maps together, and using the fused prediction map to calculate the location of the object or more than one objects at a time. On the other hand, the proper body part, e.g. brain part with a safety margin is cropped from the 3D image for 3D segmentation, wherein a 3D model is trained only for this smaller area. This approach results in significantly less false positive pixels in the segmentation and allows significantly faster model training and evaluation process.

The dataset involved two subsets (collected in separate studies). Each subset was further split to "train", "cross-val", and "test" samples which were used to train the model, to select optimal model, and evaluate the optimal model, respectively. Subset 1 (including 50 cases) was used to train the 2D localization models (30 train, 10 cross-val, 10 test). It is noted that the 2D models run on axial, sagittal, or coronal slices, so the total number of data samples were more than 10,000. Subset 2 (including 176 cases) was used to train the 3D model (111 train, 35 cross-val, 30 test). The "train", "cross-val", and "test" samples were used to optimize the model, to select an optimized model, and evaluate the optimized model, respectively. The 3D models may be also evaluated on the 10 test exams of the 2D model to allow direct comparison. Alternatively, 2D and 3D models may be trained using separate image datasets. During model training several iterations are done (using the train set). After each iteration the actual model is evaluated using the cross-val set. At the end of the training we select that version of the model that performed the best on the cross-val set, which is generally referred to in the art as the best model.

2D Convolutional Neural Networks

Figure 3:
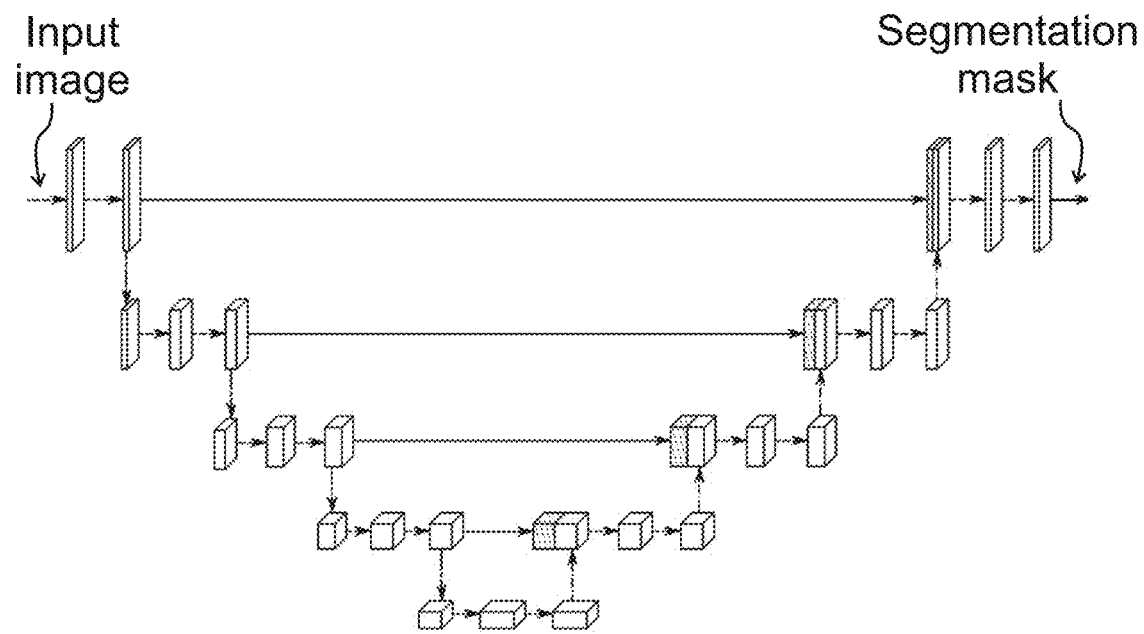
FIG. 3 illustrates a general representation of an U-Net architecture.

The subject matter disclosed herein may comprise 2D convolutional neural networks for carrying out the 2D segmentations. In this context a 2D convolutional neural network means a CNN having inputs to receive two dimensional information. In one embodiment, three 2D convolutional neural networks are used for the 2D segmentations, each of which being trained for a respective one of the first, second and third orthogonal orientations. Each of the 2D convolutional neural networks may have an U-Net architecture and may be trained by slices with the respective orientation of segmented 3D training images. The 2D U-Net model segments structures on the slices independently, i.e. not using 3D information. The U-Net architecture is known per se, e.g. from the documents referred to in the discussion of the prior art; a general representation of the U-Net architecture is depicted in FIG. 3. The network includes a contracting path and an expansive path, which gives it the u-shaped architecture. The contracting path is a typical convolutional network that includes repeated application of convolutions, each followed by a rectified linear unit and a max pooling operation. During the contraction, the spatial information is reduced while feature information is increased. The expansive pathway combines the feature and spatial information through a sequence of up-convolutions and concatenations with high-resolution features from the contracting path.

According to an example, the input of a 2D segmentation is a 128×128 single-channel matrix representing one slice of the MR image. The output is a 128×128 matrix of the 2D segmentation data, comprising prediction values being real numbers between 0 and 1, where prediction value 1 is the highest probability of the presence of the object, e.g. organ, in the corresponding voxel, and prediction value 0 is the lowest. The model (i.e. the particular architecture used in the example) applies 2 consecutive convolution filters (with 3×3 kernel) at each resolution. The number of filters is 16 at the input resolution and doubled after each pooling layer. The model has 4 pooling layers (with 2×2 pool size), so the resolution decreases to 8×8 matrix (with 256 filters) at the "bottom" of the network. Subsequently, the image is gradually upsampled to the original resolution using skip connections at each resolution level.

In the example embodiment, each 2D model was trained for 50 epochs. In each epoch 100% of positive (including the organ) and 25% of negative (not including the organ) samples were used. Due to randomization, most of the negative slices are used for training. This approach accelerates and stabilizes learning process and the accuracy of the final model is higher. Adam optimizer was used with 8 batch size and flat (0.001) learning rate.

Separate model was trained for each (axial, coronal, sagittal) orientation. The preliminary evaluation showed good segmentation result (80-90% DICE) for each model.

The combined evaluation of the three model outputs can serve a good basis for localizing the organ. After applying each model (slice-by-slice) to a 3D volume the three predictions can be fused.

Thus, three respective prediction values may be generated by the three respective 2D segmentations for voxels of the 3D medical image, and the combined evaluation comprises carrying out any of the following for the voxels:

(i) Averaging for each voxel the corresponding three prediction values.

(ii) Binarizing prediction values with a predetermined threshold value and determining voxels in which all of the corresponding three binary values represent presence of the object, e.g. all the three binarized values are "1". The predetermined threshold value can be determined on empirical basis and can be typically 0.5 or any other suitable value. Using higher/lower threshold can make the result under/over-segmented. Binarizing converts the continuous prediction values into 0 and 1 integer values.

(iii) Binarizing prediction values with a predetermined threshold value and determining voxels in which at least two of the corresponding three binary values represent presence of the object ('majority vote').

In case if the 2D segmentations are carried out in only two orthogonal orientations, two prediction values may be evaluated in combination for each respective voxel accordingly, whereby options (ii) and (iii) above will represent the same way of evaluation.

By comparing the white contours in the second and the third columns of FIG. 1, it can be seen that the combined results of the 2D segmentations provide a more accurate prediction of the presence of the organ to be segmented. This is achieved with a relatively low computational load, due to the 2D segmentation-based process.

Thus, averaging the prediction values or taking the intersection or the majority vote (after binarization) resulted in better segmentation compared to any of the 2D models. This combination of 2D models is referred to as 2.5D model in the present context.

A 3D Convolutional Neural Network with 2.5D Localization

As the organ localization with the presented 2.5D model is precise enough for various organs, and 2D models are faster than 3D CNNs, the localization information can be incorporated in the 3D model to speed up the training process and to increase the segmentation accuracy. The first piece of information is the size of the object, such as an organ (i.e. size of the bounding box 10), which may be kept constant and can be predetermined, i.e. calculated based on the whole image dataset and on other a-priori information. The second piece of information is the location (e.g., the center of the bounding box 10) of the object which can be computed from the training contour (during model training) and from the prediction of the 2.5D model (during model inferencing). Accordingly, the determining of the location of the bounding box 10 within the 3D medical image, as depicted in the first column of FIG. 2, may comprise determining a center thereof on the basis of the combined evaluation; and using dimensions thereof predetermined on the basis of at least one segmented 3D training image.

The center of the bounding box 10 may be computed in the following way: axial, coronal, sagittal segmentation models are applied to all (corresponding) slices of the input 3D medical image which results in three different segmentations of the 3D medical image;

after thresholding the axial, coronal, sagittal segmentations (using e.g. 0.5 as a threshold value) those are fused into one segmentation using e.g. majority vote or any other technique;

the largest 3D-connected component of the fused segmentation is taken; and the bounding box 10 of the largest 3D component is computed and the center of it is used as center (the size may be fixed for each organ).

During the training of the 3D model, the bounding box 10 of the organ is cut and feed into the CNN, so the input of the network is considerably smaller (e.g. 100×100×100 or 100×30×50) than the original resolution (256×256×256). To simulate the inaccuracy of the 2.5D model during the training process, the center of the bounding box 10 can be shifted with a random 3D vector (using enough safety margin to include all voxels of the organ) for each or for some of the training inputs. In contrast to the 2D model training, histogram-based intensity normalization, as well as additional mean/standard normalization was applied only to the bounding box part of the 3D medical image. Thus, the 3D convolutional neural network, that also may have a U-Net architecture, was trained by parts of segmented 3D training images, the parts corresponding in size/dimensions to the bounding box 10 used for that particular object segmentation.

In the exemplary embodiment, the architecture of the model for the 3D segmentation was selected to accommodate the 3D input, i.e. a 3D convolutional neural network was used. Here, 3D layers were used for convolution, pooling, and up sampling. In the example, the number of pooling layers were decreased to 3 (using 2×2×2 pool size). The convolutional layers use 3×3×3 kernel size. The number of filters were increased to 24 at the input resolution (and doubled after each pooling layer). The 3D model was trained for 200 epochs. In each epoch all training samples were used. The batch size was reduced to 4 due to the increased memory needs of the network. The same (Adam) optimizer and flat (0.001) learning rate was used with model selection.

During model inferencing in the example, the center of the bounding box 10 is calculated automatically, while the dimensions thereof are organ specific constants. The 3D segmentation for the object (i.e. organ) is carried out in the part of the 3D medical image corresponding to the located bounding box 10.

Results

Evaluation Framework

For each organ the models (2D axial, 2D coronal, 2D sagittal, 2.5D, 3D) were evaluated using the corresponding (2D/3D) test set. During the evaluation the same pre-process was applied, the model was applied (per slice or in bounding box 10) to the image, the prediction was binarized (using 0.5 threshold), and the result was compared with the pseudo-gold using 3D DICE metric (a statistic coefficient used to gauge the similarity of two samples).

Quantitative Evaluation

Tables I and II below demonstrate the DICE metric, which reflects the overall accuracy of the models. The paired organs were trained and tested separately (left and right part), and the results were averaged. According to the 2D results the accuracy of the axial model is the best and the sagittal model is the worst (due to over-segmentation in the other part of the brain). It is remarkable, that the 2.5D model always outperforms any of the 2D models. The 3D model is outstanding among all based on both test sets.

TABLE I 2D model results (axial, coronal, sagittal planes) for 10 test cases

|  | Amygdala | Caudate | Hippocampus | Putamen | Thalamus |
|---|---|---|---|---|---|
| Axial | 0.732 | 0.803 | 0.768 | 0.758 | 0.871 |
| Coronal | 0.685 | 0.792 | 0.743 | 0.747 | 0.850 |
| Sagittal | 0.505 | 0.554 | 0.526 | 0.535 | 0.594 |

TABLE II 2.5D and 3D model results (with 2.5D localization) for 10 and 50 test cases

|  | Amygdala | Caudate | Hippocampus | Putamen | Thalamus |
|---|---|---|---|---|---|
| 2.5D (10) | 0.782 | 0.831 | 0.809 | 0.801 | 0.889 |
| 3D (10) | 0.906 | 0.930 | 0.937 | 0.948 | 0.946 |
| 3D (50) | 0.900 | 0.931 | 0.933 | 0.944 | 0.948 |

Qualitative Evaluation

Figure 2:
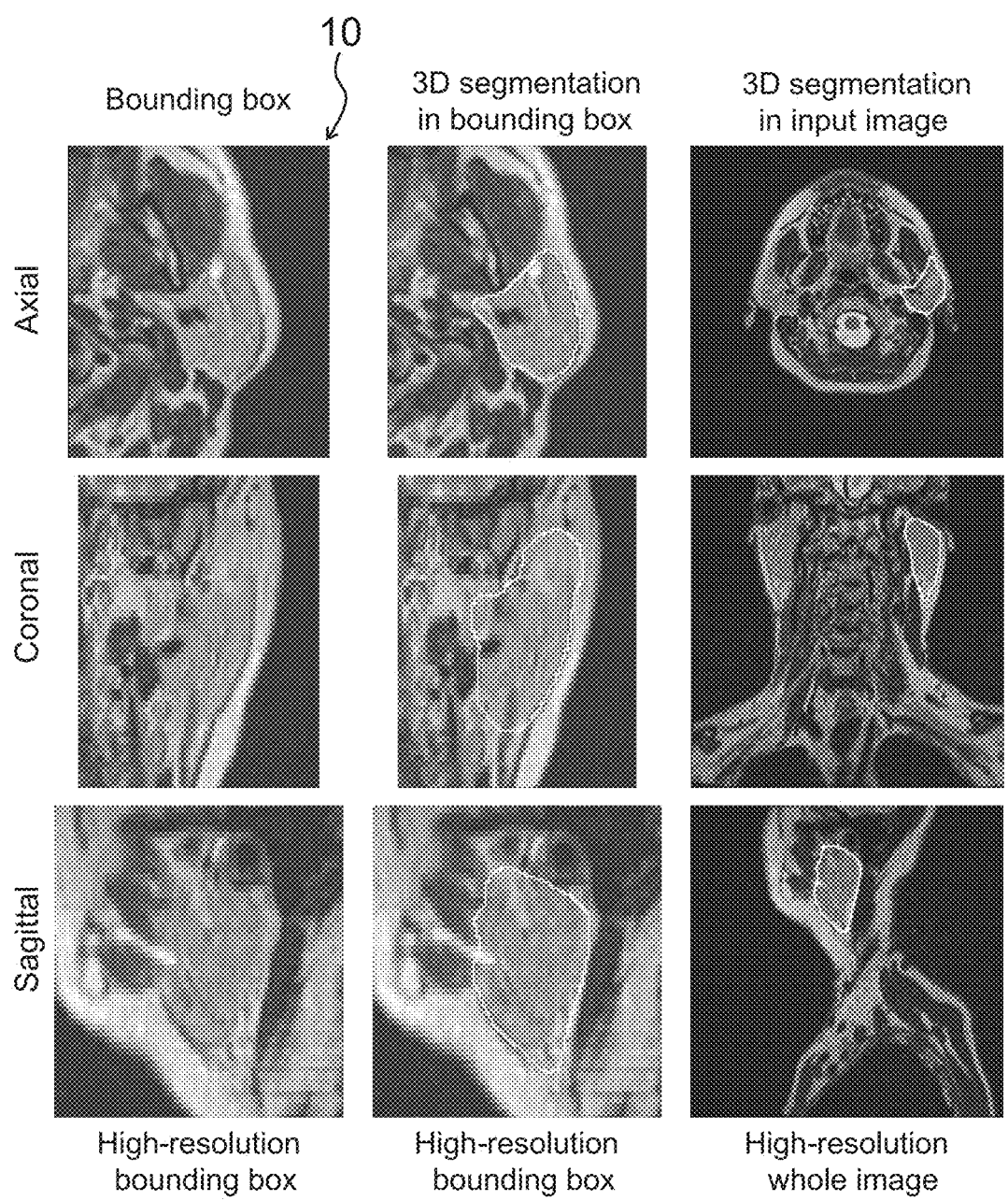
FIG. 2 illustrates a second stage of an embodiment of the automated segmentation.

FIG. 2 demonstrates the 3D results for an anatomy structure. The results of the 3D segmentation are displayed both in the bounding box 10 (second column) and in the whole 3D medical image (third column), which is the final result of the automatic segmentation method. All results are displayed in axial (left) coronal (middle) and sagittal (right) views, with white contours, only depicting the most characteristic slice. Our experiments have shown and it can be seen from the third column of FIG. 2, that the bounding-box-focused 3D segmentation resulted in an accurate result for the subject organ.

Based on the quantitative evaluation metrics the average accuracy of the 3D model was above 90% for all structures, which means the proposed method can accurately segment various structures in the brain when the localization succeeds. The case with the most localization error was an outlier from orientation point of view because the head was significantly tilted back unlike any other case in the dataset. This could be eliminated by using 3D rotation as augmentation of training data.

The average and minimal accuracy of the method according to the subject matter disclosed herein was above 90% and 80% for each organ, which is considerably higher than in prior art solutions.

In the disclosed example, an accurate brain structure segmentation was presented using the U-Net architecture. 2D models were trained to segment various structures on axial, coronal, and sagittal slices of 3D MR images. These 2D models alone cannot provide accurate 3D segmentation, but the combination of their outputs can be used for accurate localization of the bounding box of organs. The 3D models trained in this bounding box proved to be better than the state-of-the art in terms of accuracy. The presented method is especially suitable for creating a deep neural network architecture (U-Net) to segment various organs inside the brain.

The 2D and 3D models were trained and tested on HP Z440 workstation with 32 GB RAM, 12 core, 3.6 GHz CPU and GTX 1080, 8 GB RAM, 2560 CUDA cores GPU. The training of a 2D model took 20-25 minutes (per orientation) and a 3D model took 2 hours for one organ. The average segmentation time (using GPU) including the inference of three 2D models, the computation of the bounding box, and the inferencing of the 3D model was 10-15 seconds per organ per case.

Thus, a 3D U-Net model with slice-based (2D) organ localization has been developed in the example. The proposed method focuses on segmenting—e.g. for the mentioned parts of the basal ganglia—with a high accuracy (measured in DICE score), robustness and speed (for usability) to help doctors recognizing the changes inside the brain parts for detecting e.g. Alzheimer's disease. The disclosed example of the proposed method first applies 2D U-Net models to each of the three planes (axial, coronal, sagittal) to roughly segment the structure. Finally, a 3D U-Net is applied to the bounding box to segment the precise contour of the structure. For all cases the contour of various structures was defined using automated (atlas-based) tool. The evaluation demonstrated that various structures can be accurately and efficiently localized and segmented using the presented framework.

Figure 4:
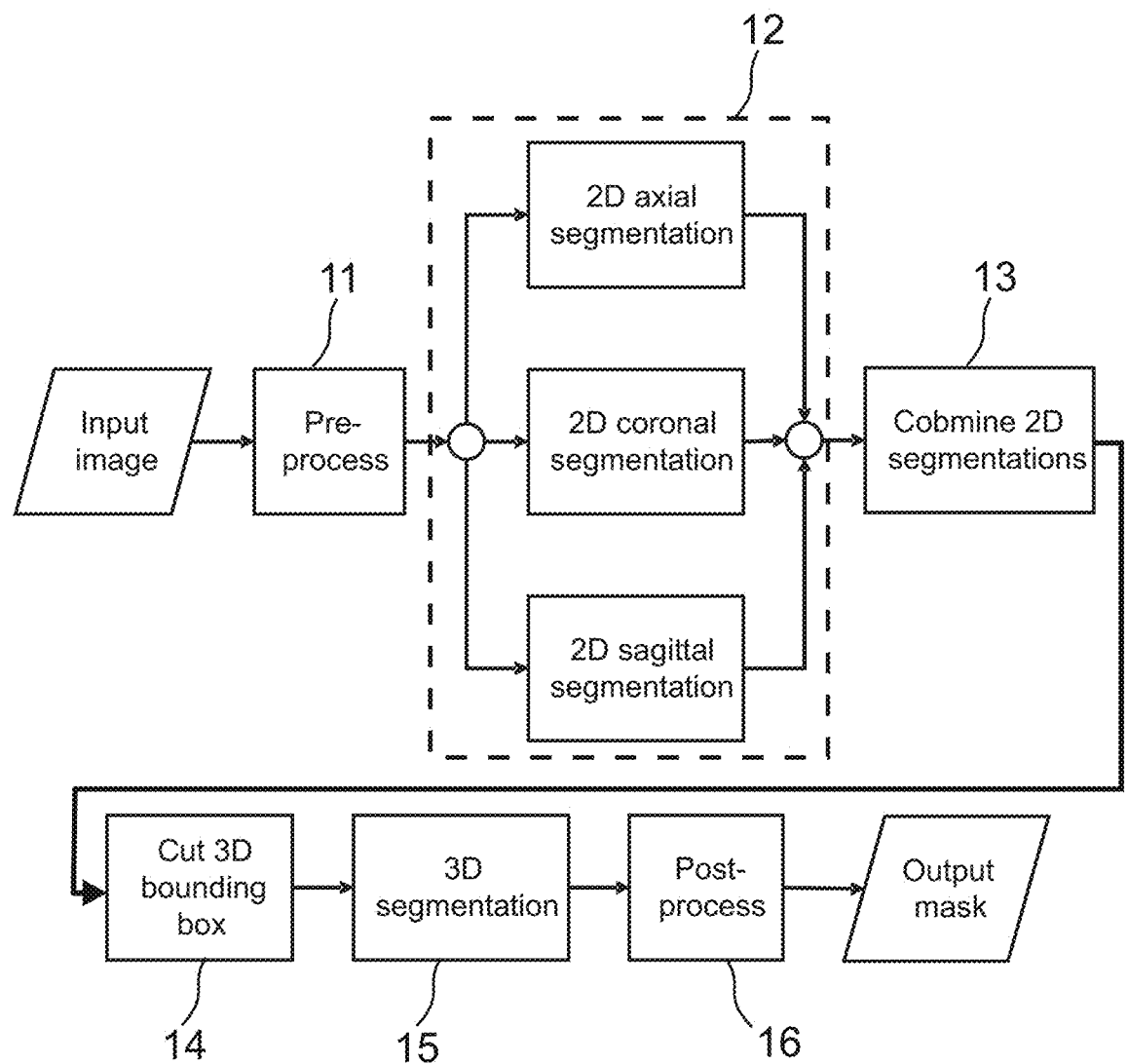
FIG. 4 illustrates a sequence of an embodiment of the method, also indicating units of an embodiment of the system.

An exemplary embodiment is a system for automatic segmentation of a medical image, the system comprising units configured to perform the steps of the above disclosed method. FIG. 4 depicts units of such a system, also illustrating stages of the method. These units can take the form of an entirely hardware embodiment, an entirely software embodiment or an embodiment including both hardware and software elements.

An input image, being a 3D medical image, is inputted into an optional preprocessing unit 11 carrying out the above mentioned preprocessing tasks. In an embodiment, preprocessing unit 11 also generates a reduced resolution 3D medical image, from which reduced resolution 2D slices can be taken for the 2D segmentations. Next, a 2D segmentation unit 12 generates the prediction values, e.g. three respective prediction values are generated by the three respective 2D segmentations for each voxel of the 3D medical image or of the reduced resolution 3D medical image. A determining unit 13 determines the location of the bounding box 10 within the 3D medical image or within the reduced resolution 3D medical image on the basis of the combined evaluation of the prediction values generated by the 2D segmentations. As mentioned above, the bounding box 10 may have dimensions which are predetermined based on the object to be segmented. Next, by a cropping unit 14 the part of the 3D medical image corresponding to the located bounding box 10 is cropped and a 3D segmentation unit 15 is applied, by using a machine learning model, to carry out a 3D segmentation for the object in the part of the 3D medical image corresponding to the located bounding box 10. Optional post processing may be carried out by post processing unit 16, e.g. for placing the segmentation into the original size 3D medical image, after which an output mask can be outputted as a result of the segmentation.

Another exemplary embodiment is a computer readable medium comprising a computer readable program for automatic segmentation of a medical image, wherein the computer readable program when executed on a computer causes the computer to perform the above disclosed method.

A technical advantage of the subject matter disclosed herein is that it enables to automatically and efficiently locate and segment organs extending in a sub-region of a larger 3D medical image, with considerably lower computational need than in prior art techniques.

This disclosure describes a method for image segmentation that is faster and equally (or more) accurate than existing state-of-the art methods. It combines 2D and 3D CNNs, such as U-Nets in a two-stage process to segment tissues. The first pass uses 2D CNNs to locate and perform a crude segmentation. Images are then cropped according to a bounding box located by the 2D segmentations, and the cropped image part is sent to a 3D CNN for a more accurate 3D segmentation. This 3D segmentation may also use information relating to the initial 2D segmentations. The method thereby uses a special combination of 2D and 3D CNNs, which may be U-Nets. The benefit is that 2D CNNs have fewer parameters and shorter inference times than 3D networks. Additionally, the 3D CNN may operate on only the most relevant portion of the image; this makes the segmentation task easier since there is less spurious tissue to recognize. While demonstrated in FIGS. 1 and 2 on the basal ganglia segmentation in MR, this method can extend to other anatomies and imaging modalities.

Apart from U-Nets, other types of CNNs can also be applied for the method, e.g. R-CNN, SegNet, VGG-16, ResNet or PSPNet. Furthermore, the 2D segmentations can be processed with a single 2D CNN trained for all of the three orientations. A further possibility is to use the same CNN for all of the 2D and 3D segmentations, with appropriate inputs. For example, a single 3D network that contains mostly 2D convolutions (in various directions) and limited 3D convolutions may solve issues addressed in this disclosure. Machine learning models other than disclosed above can also be used for the segmentation tasks.

Figure 5:
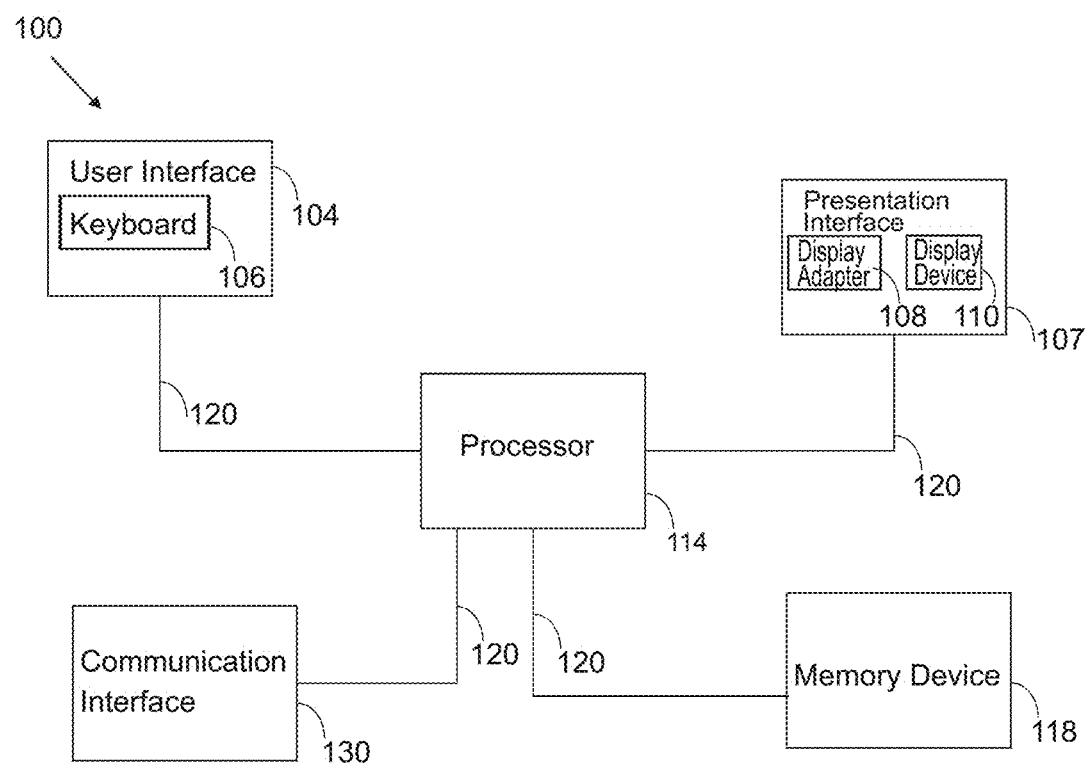
FIG. 5 is a block diagram of an exemplary computing device for carrying out the method.

An embodiment may be embodied in the form of computer-implemented processes and apparatuses for practicing those processes. FIG. 5 is a block diagram of an exemplary suitable computing device 100 for carrying out the method. In the exemplary embodiment, computing device 100 includes a user interface 104 that receives at least one input from a user. User interface 104 may include a keyboard 106 that enables the user to input pertinent information. User interface 104 may also include, for example, a pointing device, a mouse, a stylus, a touch sensitive panel (e.g., a touch pad and a touch screen), a gyroscope, an accelerometer, a position detector, and/or an audio input interface (e.g., including a microphone).

Moreover, in the exemplary embodiment, computing device 800 includes a presentation interface 107 that presents information, such as input events and/or validation results, to the user. Presentation interface 107 may also include a display adapter 108 that is coupled to at least one display device 110. More specifically, in the exemplary embodiment, display device 110 may be a visual display device, such as a cathode ray tube (CRT), a liquid crystal display (LCD), a light-emitting diode (LED) display, and/or an "electronic ink" display. Alternatively, presentation interface 107 may include an audio output device (e.g., an audio adapter and/or a speaker) and/or a printer.

Computing device 100 also includes a processor 114 and a memory device 118. Processor 114 is coupled to user interface 104, presentation interface 107, and memory device 118 via a system bus 120. In the exemplary embodiment, processor 114 communicates with the user, such as by prompting the user via presentation interface 107 and/or by receiving user inputs via user interface 104. The term "processor" refers generally to any programmable system including systems and microcontrollers, reduced instruction set computers (RISC), complex instruction set computers (CISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, memory device 118 includes one or more devices that enable information, such as executable instructions and/or other data, to be stored and retrieved. Moreover, memory device 118 includes one or more computer readable media, such as, without limitation, dynamic random access memory (DRAM), static random access memory (SRAM), a solid state disk, and/or a hard disk. In the exemplary embodiment, memory device 118 stores, without limitation, application source code, application object code, configuration data, additional input events, application states, assertion statements, validation results, and/or any other type of data. Computing device 100, in the exemplary embodiment, may also include a communication interface 130 that is coupled to processor 114 via system bus 120. Moreover, communication interface 130 is communicatively coupled to data acquisition devices.

In the exemplary embodiment, processor 114 may be programmed by encoding an operation using one or more executable instructions and providing the executable instructions in memory device 118. In the exemplary embodiment, processor 114 is programmed to select a plurality of measurements that are received from data acquisition devices.

In operation, a computer executes computer-executable instructions embodied in one or more computer-executable components stored on one or more computer-readable media to implement aspects of the invention described and/or illustrated herein. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments can take the form of an entirely hardware embodiment, an entirely software embodiment or an embodiment including both hardware and software elements. An embodiment may be implemented in software, which includes but is not limited to firmware, resident software, microcode, etc.

This written description uses examples to disclose the subject matter, including the best mode, and also to enable any person skilled in the art to practice the subject matter, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for automatic segmentation of a three dimensional (3D) medical image, the 3D medical image comprising an object to be segmented, the method characterized by comprising:
    carrying out, by using a machine learning model, in at least two of a first, a second and a third orthogonal orientation, two dimensional (2D) segmentations for the object in slices of the 3D medical image to derive 2D segmentation data;
    determining a location of a bounding box (10) within the 3D medical image based on the 2D segmentation data, the bounding box (10) having predetermined dimensions; and
    carrying out a 3D segmentation for the object in the part of the 3D medical image corresponding to the bounding box (10).

2. The method according to claim 1, characterized by using a 2D convolutional neural network for each orthogonal orientation of the 2D segmentations, each of which being trained for a respective one of the first, second and third orthogonal orientations.

3. The method according to claim 2, characterized in that each of the 2D convolutional neural networks has an U-Net architecture and is trained by slices with the respective orientation of segmented 3D training images.

4. The method according to claim 1, characterized in that the 2D segmentation data comprises prediction values representing probability of presence of the object, and determining the location of the bounding box (10) within the 3D medical image is carried out on the basis of a combined evaluation of the prediction values, wherein the dimensions of the bounding box (10) are predetermined based on the object.

5. The method according to claim 4, characterized in that a respective prediction value is generated for each respective orthogonal orientation of the 2D segmentations for voxels of the 3D medical image, and the combined evaluation comprises carrying out any of the following for the voxels:
    averaging for each voxel the corresponding prediction values;
    binarizing the prediction values with a predetermined threshold value and determining voxels in which all of the corresponding binary values represent presence of the object;
    binarizing the prediction values with a predetermined threshold value and determining voxels in which at least two of the corresponding binary values represent presence of the object.

6. The method according to claim 5, characterized in that determining the location of the bounding box (10) within the 3D medical image comprises:
    determining a center thereof on the basis of the combined evaluation; and
    using dimensions thereof predetermined on the basis of at least one segmented 3D training image.

7. The method according to claim 1, characterized by carrying out the 2D segmentations in a resolution which is reduced with respect to the full resolution of the 3D medical image.

8. The method according to claim 1, characterized by carrying out the 3D segmentation by a 3D convolutional neural network.

9. The method according to claim 8, characterized in that the 3D convolutional neural network has an U-Net architecture and is trained by parts of segmented 3D training images, the parts corresponding in size to the bounding box (10).

10. A system for automatic segmentation of a three dimensional (3D) medical image, the 3D medical image comprising an object to be segmented, the system characterized by comprising:
    a two dimensional (2D) segmentation unit (12) using a machine learning model and being configured to carry out, in at least two of a first, a second and a third orthogonal orientation, 2D segmentations for the object in slices of the 3D medical image to derive 2D segmentation data;
    a determining unit (13) configured to determine a location of a bounding box (10) within the 3D medical image based on the 2D segmentation data, the bounding box (10) having predetermined dimensions; and
    a 3D segmentation unit (15) being configured to carry out a 3D segmentation for the object in the part of the 3D medical image corresponding to the bounding box (10).

11. The system according to claim 10, characterized in that the 2D segmentation unit (12) comprises a 2D convolutional neural network for each orthogonal orientation of the 2D segmentations, each of which being trained for a respective one of the first, second and third orthogonal orientations.

12. The system according to claim 11, characterized in that each of the 2D convolutional neural networks has an U-Net architecture and is trained by slices with the respective orientation of segmented 3D training images.

13. The system according to claim 10, characterized in that the 3D segmentation unit (15) comprises a 3D convolutional neural network.

14. The system according to claim 13, characterized in that the 3D convolutional neural network has an U-Net architecture and is trained by parts of segmented 3D training images, the parts corresponding in dimensions to the bounding box (10).

15. A non-transitory computer readable medium comprising instructions which, when executed by a computer, cause the computer to carry out the method of claim 1.

* * * * *